United States Patent [19]

Vuillemenot et al.

[11] 4,289,915
[45] Sep. 15, 1981

[54] HALOGENATED POLYHYDROXY COMPOUNDS AND THEIR DERIVATIVES

[75] Inventors: Jacques Vuillemenot, Champ-sur-Frac; Edouard Grimaud, Oullins, both of France

[73] Assignee: Produits Chimiques Ugine Kuhlmann, Paris, France

[21] Appl. No.: 182,189

[22] Filed: Sep. 20, 1971

Related U.S. Application Data

[63] Continuation-in-part of Ser. No. 776,805, Nov. 18, 1968, abandoned, and a continuation-in-part of Ser. No. 346,078, Feb. 20, 1964, abandoned, and Ser. No. 668,644, Sep. 18, 1967, abandoned.

[51] Int. Cl.³ .......................................... C07C 43/225
[52] U.S. Cl. ................................. 568/609; 568/643; 568/47; 560/194; 252/188.3 R; 525/42
[58] Field of Search ............... 260/613 R, 613 B; 568/609

[56] References Cited

U.S. PATENT DOCUMENTS

| | | | |
|---|---|---|---|
| 2,130,526 | 9/1938 | Coleman et al. | 260/613 R |
| 2,130,527 | 9/1938 | Coleman et al. | 260/613 R |
| 2,615,823 | 10/1952 | Lawlor et al. | 260/613 R |
| 3,056,843 | 10/1962 | Wismer | 260/613 R |
| 3,102,105 | 8/1963 | Collardeau et al. | 260/613 R X |
| 3,227,683 | 1/1966 | Schulte-Huermann et al. | 260/613 R X |

FOREIGN PATENT DOCUMENTS

| | | | |
|---|---|---|---|
| 1357100 | 2/1964 | France | 260/613 R |
| 1012328 | 12/1965 | United Kingdom | 260/613 R |

*Primary Examiner*—Bernard Helfin
*Attorney, Agent, or Firm*—Pennie & Edmonds

[57] ABSTRACT

This invention relates to halogenated polyhydroxy compounds of the formula $$Ar\text{\textlbrackdbl}OR(OH)_{n-1}\text{\textrbrackdbl}_m$$

wherein Ar is a halogenated polyphenyl or halogenated polyphenylbenzene containing 2 to 5 aromatic rings with each of said rings having at least 3 halogen atoms thereon, R is an aliphatic hydrocarbon, an aliphatic ether or an alicyclic hydrocarbon containing 2 to 40 carbon atoms and n and m each is an integer 2, 3 or 4 and when R is a saturated aliphatic hydrocarbon n and/or m is 3 or 4.

This invention also relates to a process for preparing halogenated polyhydroxy compounds of the formula $$Ar\text{\textlbrackdbl}OR(OH)_{n-1}\text{\textrbrackdbl}_m$$

wherein Ar is a halogenated polyphenyl or halogenated polyphenylbenzene containing 2 to 5 aromatic rings with each of said rings having at least 3 halogen atoms thereon, R is an aliphatic hydrocarbon, an aliphatic ether or an alicyclic hydrocarbon containing 2 to 40 carbon atoms and n and m each is an integer 2, 3 or 4 which comprises:

(a) reacting in a temperature range between about 80° and 230° C., a halogenated polyphenyl or halogenated polyphenylbenzene containing 2 to 5 aromatic rings with each of said rings having at least 4 halogen atoms thereon, in the presence of an acid acceptor with an alcohol of the formula $$R(OH)_n$$

wherein R is an aliphatic hydrocarbon, an aliphatic ether or an alicyclic hydrocarbon containing 2 to 40 carbon atoms and n is 2, 3 or 4; and (b) removing from the reaction medium the halogenated polyhydroxy compound.

1 Claim, No Drawings

HALOGENATED POLYHYDROXY COMPOUNDS AND THEIR DERIVATIVES

CROSS REFERENCE TO RELATED APPLICATION

This application is a continuation-in-part application of our co-pending application Ser. No. 776,805, filed Nov. 18, 1968 now abandoned and of our application Ser. No. 346,078, filed Feb. 20, 1964, now abandoned, and of our application Ser. No. 668,644 filed Sept. 18, 1967, now abandoned.

BACKGROUND OF THE INVENTION

I. Field of the Invention

This invention relates to halogenated polyhydroxy compounds having a structure represented by the formula

Ar[OR(OH)$_{n-1}$]$_m$ in which Ar is a halogenated polyphenyl or a halogenated polyphenylbenzene containing 2 to 5 aromatic rings with each of said rings having at least 3 halogen atoms thereon, R is an aliphatic hydrocarbon, an aliphatic ether or an alicyclic hydrocarbon containing 2 to 40 carbon atoms and n and m each is an integer 2, 3 or 4 and when R is a saturated aliphatic hydrocarbon n and/or m is 3 or 4.

This invention further pertains to a process for manufacturing these halogenated polyhydroxy compounds including those wherein R is a saturated aliphatic hydrocarbon and n and/or m is 2 and the polyester derivatives of said halogenated polyhydroxy compounds.

II. Description of the Prior Art

Collardeau et al. in U.S. Pat. No. 3,102,105 disclose compounds of the formula

Ar[OR(OH)]$_2$ wherein Ar is a diphenyl radical containing a total of 6 to 8 chlorine atoms and R is a ethylene or propylene radical. Accordingly, the Collardeau et al. compounds are limited to but two reactive hydroxyl groups.

It is often advantageous in the preparation of polyhydroxy derivatives to have available a greater number of reactive hydroxyl groups in the starting alcohol than the two hydroxyl groups provided by the Collardeau et al. compounds, as for example, when it is desirable to obtain highly reticulated polymers exhibiting greater mechanical strength and resistance to combustion. There are, moreover, no structural features in the Collardeau et al. dihydroxy compounds which would tend to enhance the reactivity of the hydroxyl groups thereby offsetting to some degree the disadvantages flowing from the presence of just two such groups.

Wismer in U.S. Pat. No. 3,056,843 discloses a process in which perhalogenated benzene is reacted with polyol to produce a hydroxylated compound of the formula

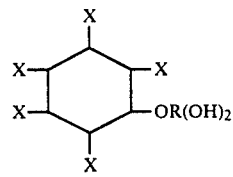

wherein X is a halogen radical and R is an alkylene group. Wismer discovered in his reaction that regardless of the ratio in which the reactants are charged the primary reaction consists in the removal of a single halogen atom from the hexahalobenzene in the reaction. The hydroxylated polyhalobenzene thus obtained can be reacted with diacids to produce linear polyesters which, due to the high halogen content, have desirable fire self-extinguishing properties in many commercial polymeric and coating applications.

The single substitution reaction of Wismer however, necessarily limits the number of reactive hydroxyl groups that can be introduced into the aromatic ring and hence prevents the use of the resultant hydroxy compound for the preparation of highly reticulated polymers which would have greater strength and fire resistant properties.

SUMMARY OF THE INVENTION

Halogenated polyhydroxy compounds have been prepared with two and as many as twelve hydroxyl groups which are available as reactive sites for the preparation of derivatives demonstrating highly advantageous properties as hereinafter disclosed. Moreover, it has been discovered that when said compounds possess but two hydroxyl groups, the presence of a hereto oxygen atom or unsaturation in the aliphatic radical R, tends to increase the reactivity of the hydroxyl groups, thus compensating in some measure for there being only two hydroxyl sites available for reaction.

We have also discovered that halogenated polyhydroxy compounds containing two and as many as twelve hydroxy groups in different ring positions of an aromatic compound can be simply and effectively prepared by the process of this invention. Broadly stated, the present process comprises:

(a) reacting in a temperature range between about 80° and 230° C., a halogenated polyphenyl or halogenated polyphenylbenzene containing 2 to 5 aromatic rings with each of said rings having at least 4 halogen atoms thereon, in the presence of an acid acceptor with an alcohol of the formula

R(OH)$_n$ wherein R is an aliphatic hydrocarbon, an aliphatic ether or an aliphatic thio-ether or an alicyclic hydrocarbon containing 2 to 40 carbon atoms and n is 2, 3 or 4; and (b) removing from the reaction medium the halogenated polyhydroxy compound.

Advantageously, the reaction is carried out in an inert solvent using an excess amount of polyol, preferably in the range between 2 to 30 times the amount required. The polyol used may be an alkyl, an alkenyl, a cycoalkyl or a cycloalkenyl polyhydroxyl compound containing 2 to 40 carbon atoms. The polyols containing ether or thioether linkages as well as those having one or more double bonds are also useful in the process of this invention.

The halogenated polyhydroxy compounds of this invention can be used to react with saturated or unsaturated polycarboxylic acids to produce new polyesters which, due to the high halogen content and available reactive -OH groups, have a remarkable fire self-extinguishing property, high resistance to chemical agents, good reactivities and good mechanical properties at both high and low temperatures. The polyhydroxy compounds of this invention exhibit all of the properties of polyols and, therefore, may be used for the preparation of, in addition to polyesters, polyurethanes, epoxy resins, mono- and polyphosphites, etc. These new products also enjoy the desirable physical properties contributed by the polyhydroxy compounds of this invention.

DESCRIPTION OF THE PREFERRED EMBODIMENTS

In preparing the halogenated polyhydroxy compounds of this invention, the reaction of the halogenated polyphenyl or halogenated polyphenylbenzene and the polyol involves the condensation of one terminal aromatic ring to one hydroxyl of the polyol. The other -OH group or groups remain free, thus available for further reaction for the preparation of polyesters and the like and contribute to the polyol characteristics of the resultant polyhydroxy compounds of this invention.

As stated previously, the suitable halogenated polyphenyls or halogenated polyphenylbenzenes have two to five aromatic rings each of which has three or more halogen atoms. Advantageously, the polycyclic compounds have two to three aromatic rings and are perhalogenated. Examples of halogenated polycyclic compounds which are useful in the process of this invention include halogenated compounds derived from 1,3-diphenylbenzene, 1,3,5-triphenylbenzene, 1,2,3-triphenylbenzene and 1,2,4,5-tetraphenylbenzene. In addition, the following halogenated polycyclic compounds can also be used:

(a) hexa-, hepta- and nonachlorodiphenyl;
(b) nona-, deca-, undeca-, dodeca-, tridecachloroterphenyl;
(c) dodecachloro quaterphenyl, etc. . . . up to perchloroquaterphenyl which contains 18 chlorine atoms; and
(d) dodecachlorotriphenylbenzene . . . etc., up to perchlorotriphenylbenzene which contains 18 chlorine atoms.

Equally suitable are the brominated, fluorinated, and iodated derivatives of these compounds in groups (a), (b), (c) and (d).

Advantageously, the halogenated substituent on these halogenated compounds is chlorine. A perhalogenated polyphenyl of particular interest is decachlorodiphenyl, which can be produced economically using a process described in French patent No. 1,229,815, March 10, 1959, assigned to the assignee hereof. The hydroxy groups advantageously are primary hydroxyls. Examples of such polyols include trimethylol ethane, trimethylol propane, trimethylol hexane, and trimethylol heptane.

The R in the polyols may also contain one or more ether or thioether linkages as well as one or more double bonds. Examples of polyols of this type include glycols which contain $-R_1-(O-R_2)_q-$ linkages wherein $R_1$ and $R_2$ are alkylene and q is an integer from 1 to 20. Typical glycols that have been found to be eminently suitable are di-, tri-, tetra- and polyethylene glycols of which molecular weight may be as high as 1000.

Other suitable polyols may include 1,2,6-hexanetriol, glycerol, sorbitol, the mono-, di-, and tri-pentaerythritols, ethylene glycol, propylene glycol, hydroquinone, pyrogallol, resorcinol, 1,6-hexanediol, 1,5-pentane diol, butene diols, propoxylated butene diols, 3-cyclohexene-1,1-dimethanol and monoallyl ether of trimethanol.

More specifically, polyols that contain one or more double bonds and thioether linkages that can be used are as follows:

I. Polyols containing double bonds 1-butene-3,4 diol (erythrol); 2-butene-1,4 diol; 2-hydroxymethyl propene-2-ol; 1-pentene-3,4 diol; 2-pentene-1,4 diol; 2-pentene-4,5 diol; 1-propene-1,2diol; 1-butene-1,3 diol; 2-butene-1,3 diol; 1-butene-1,4 diol; 2-butene-1,4 diol.

II. Polyols containing thioether linkage

Thiodiglycol; 2-hydroxyethyl and 3-hydroxypropyl sulfide; trithioglycol; ethylene bis-2-mercaptoethylsulfide; ethylene bis-2-hydroxyethysulfide.

The solvent which can be used must be substantially inert and capable of at least partially dissolving the reactants employed, namely, polyhalogenated polyphenyl or polyhalogenated polyphenylbenzene, and the polyols. Advantageously, the solvents have boiling points sufficiently high to make it possible to use a reaction temperature that will produce a satisfactorily high reaction rate. Among acceptable solvents include benzene, mono-, di-, and tri-chlorobenzene.

Other solvents which may be used include ethers, such as dimethoxy methane, dimethoxy ethane, dioxane; acetals, such as diethylacetal, dipropylacetal; and amides such as dimethylformamide.

Selection of suitable acid acceptors of the hydrohalogen acid produced by the condensation may be made from either basic mineral products, such as sodium or potassium hydroxides, and alkaline carbonates, or from organic bases, such as pyridine.

The quantities of hydrohalogen acid acceptor to be used depend on the nature of the halogenated polyphenyl or polyphenylbenzene being employed and on the number of halogen atoms which are to be substituted. In general, we employ one mole of base per terminal phenyl nucleus and a large excess of polyol, the excess being from 2 to 30 times the stoichiometric quantity.

The process for producing halogenated polyhydroxy compounds in accordance with the invention may be accomplished by placing the various reactants and the solvent in a reaction vessel, and the reaction mixture maintained at a reflux condition for several hours. After cooling, the precipitated salt, which is the by-product of the reaction, is filtered, together with the unreacted polyhalogenated polyphenyl or polyhalogenated polyphenylbenzene, both of which are insoluble in the solvent.

The solvent which contains the dissolved halogenated polyhydroxy compound of this invention is then removed by distillation and the residue is washed with an acidulated water and then with a regular unacidulated water. When the polyol used is soluble in water, washing in such a manner removes the unreacted polyol and also the salt (e.g., NaCl) formed.

The halogenated polyhydroxylated compounds of this invention thus obtained may react with saturated or unsaturated organic acids to produce new polyesters characterized by a high halogen content.

Further to illustrate this invention, specific non-limitative examples are described hereinbelow. In these examples, "A" represents the molar ratio of NaCl formed during the condensation reaction to the polyol consumed in the reaction. When this ratio is equal to or near unity, it proves that the condensation reaction involved only one -OH of the polyol.

The reaction products produced in these examples were in the form of a mixture of various isomers, the separation of which was not made.

EXAMPLE 1

Preparation of bis-[2,2,-di-(hydroxymethyl)-1butoxyl]-octachlorodiphenyl, the structure of which may be represented by the following formula

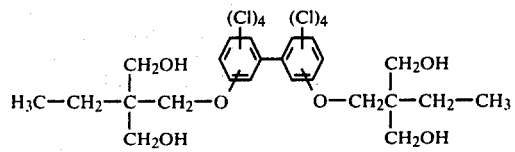

The reaction scheme may be represented by the following general equations:

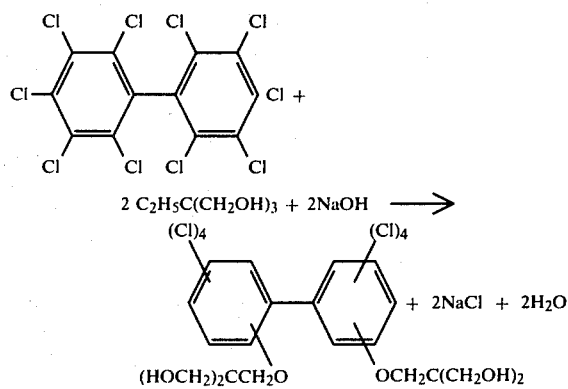

The following compounds were introduced into a reaction vessel having a five liter capacity equipped with a mixer and a condenser:
1500 grams (3 moles) of decachlorodiphenyl
840 grams (6 moles) of trimethylol propane
246 grams (6.15 moles) of sodium hydroxide
3000 cc. of dioxane The reaction mixture was heated to reflux and was held at that temperature with continuous stirring for 18 hours. After cooling, a solid and the dioxane solution were separated by filtration. The solid was then dissolved in water and the aqueous solution thus obtained was adjusted to 5000 cc. volume. The amount of sodium chloride in the solution was determined by titration with silver nitrate and was found to be equal to 337 grams. The dioxane solution was found to be alkaline. In order to bring it to a neutral pH, it was necessary to add 0.33 moles of HCl. The solution was then filtered and the dioxane was separated from the filtrate by distillation yielding 2076 grams of a yellow solid product having a melting point below 100° C. and possessing the following characteristics:

41.3% chlorine (as compared with a calculated or predicted value of 40.9)
OH index 316 (as compared with a calculated value of 323)
molecular weight as determined by cryoscopy in benzene; 655 (compares to a calculated value of 694)
The yield thus appeared as follows: product yield 99.2% yield in sodium chloride 96.0%
The quantity of sodium hydroxide consumed amounted to 97.5% of the theoretical quantity.

EXAMPLE 2

250 parts of decachlorodiphenyl (0.5 mole), 1325 parts of diethylene glycol (12.5 moles) and 1050 parts of monochlorobenzene were introduced into a reactor having a rotating stirring device.

The reaction mixture was raised to the boiling point of monochlorobenzene, i.e., about 130° C., in a nitrogen atmosphere whereupon 40 parts of NaOH (1 mole) dissolved in 75 parts of water were added over a period of 30 minutes while the mixture was being stirred.

The reaction was allowed to proceed while the water which had been introduced as well as the water formed were extracted until the NaOH disappeared, which required about 2 hours. The mixture was then chilled and the reaction product was first washed with acidulated water and then with pure water. Thereupon the aqueous layer was separated from the organic layer by decanting and the organic layer was then washed again with water to eliminate excess diethylene glycol and sodium chloride.

After the solvent was evaporated, the reaction yielded 293 parts of a yellowish orange resin which was transparent and which had the following properties:
ring and ball softening point: 50°-53° C.
OH index: 181
Chlorine content: 51%
A=(1.32/1.32)=1.
The principal constituent of the resin was bis(tetrachlorophenoxy ethoxy-ethanol).

EXAMPLE 3

The following compounds were introduced into a reactor equipped with a mixer:
250 parts of decachlorodiphenyl (0.5 mole)
1875 parts of triethylene glycol (12.5 moles)
1040 parts of monochlorobenzene.

The reaction mixture was raised to the boiling point of monochlorobenzene in a nitrogen atmosphere. Then 56 parts (1 mole) of NaOH dissolved in 75 parts of water were added slowly thereinto over a period of 30 minutes, the mixture being meanwhile vigorously stirred.

The mixture was then processed as in Example 2 and 345 parts of a liquid resin was obtained which was rather viscous, brown in color and had the following characteristics:
Chlorine content: 41%
OH index: 140
A=1.76/1.74=1.01
The liquid resin comprised principally bis-tetrachlorophenoxy-ethoxy-ethanol).

EXAMPLE 4

The following compounds were introduced into a reactor equipped with a mixer:
250 parts of decachlorodiphenyl (0.5 mole)

2500 parts of tetraethylene glycol (12.5 moles)
1040 parts of monochlorobenzene.

The reaction mixture was raised to the boiling point of monochlorobenzene in a nitrogen atmosphere. Then 40 parts of NaOH (1 mole) dissolved in 75 parts of water was added thereto over a period of 30 minutes while the mixture was being vigorously mixed.

The mixture was then treated in accordance with the procedure of Example 2 and 391 parts of an orange-colored resin were obtained which was a viscous liquid and had the following characteristics:
Chlorine content: 35%
OH index: 123
$A = 1.75/1.73 = 0.955$.

EXAMPLE 5

The following compounds were introduced into a reactor having a mixer:
250 parts of decachlorodiphenyl (0.5 mole)
1675 parts of dipropylene glycol (12.5 moles)
1040 parts of monochlorobenzene The reaction mixture was raised to the boiling point of monochlorobenzene in a nitrogen atmosphere. Then 40 parts of NaOH (1 mole) dissolved in 75 parts of water were added over a period of 30 minutes, the mixture being meanwhile well stirred.

The procedure of Example 2 was then followed and 320 parts of a yellowish-orange resin were obtained which was a viscous liquid and had the following characteristics:
Chlorine content: 45.5%
OH index: 156
$A = 1.44/1.47 = 0.98$.

EXAMPLE 6

The following materials were charged into a reactor having a rotating stirrer:
250 parts of decachlorodiphenyl (0.5 mole)
1325 parts of diethylene glycol (12.5 moles)
1040 parts of monochlorobenzene
40 parts of NaOH (1 mole) in the form of sticks or straws.

The reaction mixture was raised to the boiling point of monochlorobenzene, in a nitrogen atmosphere and was allowed to react for 2 hours while the water formed in the reaction was being removed. The subsequent steps were those set forth in Example 2.

After elimination of the solvent, 288 parts of a very clear yellow resin were obtained which was transparent in nature and had the following characteristics:
Ring and Ball softening point: 51°–54° C.
Chlorine content: 51.5%
OH index: 181
$A = 1.34/1.36 = 0.99$

EXAMPLE 7

The following compounds were introduced into a reactor having a rotating stirrer:
250 parts of decachlorodiphenyl (0.5 mole)
1675 parts of dipropylene glycol (12.5 moles)
1240 parts of orthodichlorobenzene
40 parts of NaOH (1 mole) in the form of thin sheets.

The mixture was raised to the boiling point of orthodichlorobenzene i.e., 180° C., in a nitrogen atmosphere. At this temperature the sodium hydroxide had completely disappeared. The subsequent operating steps were those set forth in Example 2.

After elimination of the solvent by evaporation under a vacuum of 15 mm. Hg, 310 parts of a yellow resin were obtained which was a viscous liquid and had the following characteristics:
Chlorine content: 45%
OH index: 135
$A = 1.49/1.5 = 0.995$

EXAMPLE 8

The following materials were introduced into a reactor having a rotating stirrer:
250 parts of decachlorodiphenyl (0.5 mole)
292 parts of propoxylated butene diol (2 moles)
40 parts of NaOH (1 mole) in the form of thin sheets
720 parts of monochlorobenzene.

The reaction mixture was refluxed and raised to the boiling point of monochlorobenzene, while the water formed was being extracted. After 1 hour and 45 minutes of reaction, the sodium hydroxide had disappeared entirely. The remaining operating steps were similar to those set forth in Example 2.

After evaporation of the solvent, 296 grams of a brown resin were obtained which had the following characteristics:
Ring and Ball softening point: 57°–60° C.
Chlorine content: 52%
OH index: 231
$A = 0.8/0.9 = 0.89$

EXAMPLE 9

The following compounds were introduced into a reactor having a rotating stirrer:
107 parts of perchlorated terphenyl (0.15 mole)
560 parts of triethylene glycol (3.7 moles)
310 parts of monochlorobenzene
12 parts of NaOH in the form of thin sheets (0.3 mole)

The liquid was raised to its boiling point in a nitrogen atmosphere and the reaction was allowed to proceed for one hour while the water formed was removed. The subsequent operating steps were similar to those of Example 2.

133.5 parts of a clear, yellowish resin were obtained which were soft and had the following characteristics:
Ring and Ball softening point: 46°–49° C.
Chlorine content: 46%
OH index: 109
$A = 0.91/0.91 = 1$

EXAMPLE 10

The following compounds were introduced into a reactor having a rotating stirrer:
215 parts of octochlorodiphenyl (0.5 mole)
1875 parts of triethylene glycol (12.5 moles)
40 parts of NaOH (1 mole) in the form of thin sheets
1222 parts of orthodichlorobenzene.

The mixture was refluxed and raised to the boiling point of orthodichlorobenzene, i.e., 180° C. while the water formed was extracted therefrom. After two hours of reaction, the sodium hydroxide had entirely disappeared. The subsequent operating steps were similar to those of Example 2.

After evaporation of the solvent, 307 parts of a yellowish and viscous liquid resin were obtained which had the following characteristics:
Chlorine content: 35%
OH index: 185
$A = 0.9/0.9 = 1$

EXAMPLE 11

The following compounds were introduced into a reactor having a rotating stirrer:
62.5 parts of decachlorodiphenyl (0.125 mole)
3125 parts of polyethylene glycol of molecular weight 1000 (3.125 moles)
10 parts of NaOH (0.25 mole) in straws
260 parts of monochlorobenzene.

The reaction mixture was refluxed and raised to the boiling point of monochlorobenzene while the water formed was withdrawn therefrom. After 2 hours of reaction, the sodium hydroxide had entirely disappeared. The remaining operating steps wer similar to those of Example 2. After evaporation of the solvent, 294 parts of a clear, yellowish resin were obtained which was a liquid and had the following characteristics:
Chlorine content: 12.1%
OH index: 46
A = 0.24/0.24 = 1

EXAMPLE 12

This example pertains to the preparation of a polyester.

There were introduced into a reactor having a stirrer the following: 674 parts (0.7 mole) of the product obtained in Example 2. This was heated in a nitrogen atmosphere to 120° C. There were then introduced still under the nitrogen atmosphere and with vigorous mixing the following:
95 parts of propylene glycol (0.23 mole) and
196 parts of maleic anhydride (2 moles).

The mixture was raised to 150° C. and then further raised to 180° C. over a period of four hours. It was held at this temperature for four more hours while the water formed was extracted therefrom. When 7/8 of the free hydroxyls had been esterified, the remaining water contained in the reacting mixture was removed under a vacuum, and the mix was then cooled.

A non-saturated clear, yellowish color polyester containing 36.5% chlorine and 0.209% of double bonds was obtained.

A mixture was made up which comprises 64.0 parts of the polyester thus produced, 36 parts of styrene and 70 ppm of hydroquinone as a stabilizer.

A solution was obtained having a viscosity of 165 cps of 20° C. and a chlorine content of 30%. Hardening was then effected according to the prescriptions of the SPI tests. The polymerization temperature of 205° C. was obtained in 8 minutes. The hardened resin had a Barcol hardness of 50.

A reinforced structure of glass polyester fibers was then prepared by using 22 parts of the styrene solution above-mentioned for 10 parts of glass. A reinforced product was then produced which was colorless and had excellent self-extinguishing properties according to the ASTM test D653 and also corresponding to a figure merit of 10,000 according to the test BS476 (second part, 1955).

EXAMPLE 13

Into a reactor equipped with a system of agitation, there were charged 285 parts of the product prepared in Example 2 (equivalent to 0.3 mole). Melting was done at 120° C. under nitrogen. There were then added 43.8 parts of adipic acid (0.3 mole) and 13.4 parts of trimethylolpropane (0.1 mole). The temperature was raised to 150° C. in the course of 1 hour, and the temperature was then raised by 10° C. per hour, to reach 190° C. after 5 hours.

After 15 hours of esterification at this temperature, the mixture was placed under vacuum and 10 parts of water and 332.2 parts of a light yellow-orange product were collected; the properties of the product were as follows:
Softening point: 90° C.
Chlorine content: 44%
OH: 1.40%
Acid index: 26 (corresponding to the acidity of the OH in phenolics).

EXAMPLE 14

In a reactor equipped with a system of agitation, there were placed 190 parts of the product prepared in Example 1 (equivalent to 0.2 mole). Melting was done under nitrogen at 120° C., and there was added 9.8 parts of maleic anhydride (0.1 mole) and 16.6 parts of phthalic anhydride (0.1 mole). The temperature was raised to 150° C. in the course of 1 hour, and the temperature was then raised by 10° C. per hour to reach 180° C. after 4 hours.

After 3 hours of reaction at 180° C., the mixture was placed under vacuum and 3.4 parts of water were collected, the acidity introduced by the anhydrides being lowered by 7/8. There were thus obtained 213 parts of a transparent light yellowish resin having the following properties:
Softening point: 95° C.
Chlorine content: 45.5%
Acid index: 43
Double bonds: 0.047%

EXAMPLE 15

The following compounds were added into a reactor equipped with a rotary stirrer:
50 parts of decachlorodiphenyl
355 parts of 3-cyclohexene 1-1 dimethanol
260 parts of orthodichlorobenzene
8 parts of thin pieces of NaOH The liquid was brought to boiling (about 180° C.) under nitrogen and was allowed to react for 30 minutes while withdrawing the water thus formed. Thereafter the solvent, orthodichlorobenzene, was removed by evaporation and the residue was leached with acidulated water then with pure water.

After drying a yellowish resin with the following characteristics was recorded:
Chlorine content: 40%
OH index: 150
Ring and Ball
softening point: 69°–72° C.
A = 0.845/0.9 = 0.94.

EXAMPLE 16

The following compounds were added to a reactor equipped with a rotary stirrer:
50 parts of decachlorodiphenyl
305 parts of thioglycol
260 parts of orthodichlorobezene
8 parts of thin sheets of NaOH The liquid was brought to boiling at about 180° C. in a nitrogen atmosphere. The reaction was allowed to proceed under these conditions for 2 hours and 30 minutes, while the water thus formed was removed. The subsequent process steps were carried out similar to those described here. The resin obtained had a chestnut color. A total of 57 parts of resin were obtained. The resin had 58.7% to 57.5% of chlorine and had an OH index of 115.

EXAMPLE 17

1000 parts of the product produced in Example 2 were used to prepare a polyester with 98 parts of maleic anhydride. The chlorinated polyhydroxy compound prepared in Example 2 was initially introduced into a reactor equipped with a rotary stirrer and was heated under a nitrogen atmosphere to 120° C. After the reactant reached 120° C., maleic anhydride was introduced thereinto, while the reactant mixture was being vigorously agitated. The temperature of the reactant mixture was raised first to 150° C. and then progressively to 180° C. within a four-hour period. The reaction was maintained at this temperature for an additional four-hour period while withdrawing therefrom the water thus formed from the reaction. After about 7/8 of the alkylhydroxy groups have been esterified, any water remaining in the reactor was siphoned off, and the reaction mixture was cooled to about room temperature. An unsaturated polyester having a pale yellow color containing 46.7% chlorine and 0.09 ethylene group per 100 grams was obtained.

65 parts of the polyester thus obtained was mixed with 35 parts of styrene and 70 ppm hydroquinone which was used as a stabilizer to form a polymeric solution having a viscosity of 165 cps at 20° C. and a chlorine content of 30%. A reinforced article was prepared with this polymeric solution using 22 parts of solution to 10 parts of a glass fibrous mat. The article had noteworthy self-extinguishing properties according to the ASTM D653 test and a self-extinguishing coefficient of 10,000 according to the BS 476 test (2nd part, 1955).

We claim:

1. A compound consisting essentially of bis(tetrachlorophenoxy ethoxy-ethanol) and having the structure

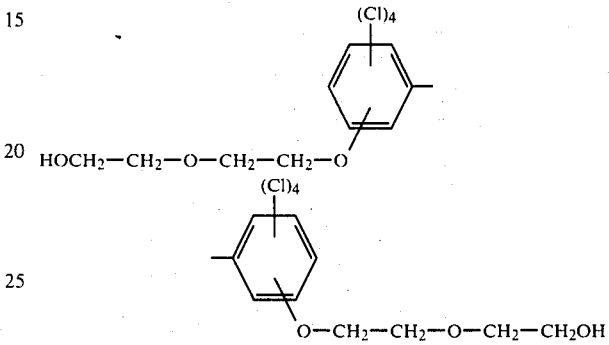

* * * * *

UNITED STATES PATENT AND TRADEMARK OFFICE
CERTIFICATE OF CORRECTION

PATENT NO. : 4,289,915
DATED : September 15, 1981
INVENTOR(S) : Jacques Vuillemenot and Edouard Grimaud It is certified that error appears in the above-identified patent and that said Letters Patent are hereby corrected as shown below:

Column 2, line 35, reads "a hereto oxygen", should read
--a hetero oxygen--

Column 2, line 25, reads "greater strength", should read
--much greater strength--

Signed and Sealed this

Twenty-ninth Day of December 1981

[SEAL]

Attest:

GERALD J. MOSSINGHOFF

Attesting Officer　Commissioner of Patents and Trademarks